US008377714B2

(12) United States Patent
Cole-Hamilton et al.

(10) Patent No.: US 8,377,714 B2
(45) Date of Patent: Feb. 19, 2013

(54) CONJUGATED NANOPARTICLES AND THEIR USE IN DETECTION OF LATENT FINGERPRINTS

(75) Inventors: David John Cole-Hamilton, St Andrews (GB); Ifor David William Sámuel, St Andrews (GB); Jennifer Rachel Amey, St Andrews (GB); John William Bond, Northampton (GB)

(73) Assignee: The University Court of the University of St Andrews, St Andrews (GB)

( * ) Notice: Subject to any disclaimer, the term of this patent is extended or adjusted under 35 U.S.C. 154(b) by 54 days.

(21) Appl. No.: 12/997,417

(22) PCT Filed: Jun. 18, 2009

(86) PCT No.: PCT/GB2009/050699
§ 371 (c)(1),
(2), (4) Date: Jan. 13, 2011

(87) PCT Pub. No.: WO2009/153599
PCT Pub. Date: Dec. 23, 2009

(65) Prior Publication Data
US 2011/0104815 A1     May 5, 2011

(30) Foreign Application Priority Data

Jun. 18, 2008  (GB) .................................. 0811170.0

(51) Int. Cl.
*G01N 21/76* (2006.01)
(52) U.S. Cl. ........ 436/172; 436/532; 438/403; 438/404; 977/902

(58) Field of Classification Search ........................ None
See application file for complete search history.

(56) References Cited

U.S. PATENT DOCUMENTS

| 6,306,662 | B1 | 10/2001 | Menzel | |
|---|---|---|---|---|
| 2007/0140974 | A1* | 6/2007 | Torres et al. ............... | 424/9.323 |
| 2008/0096289 | A1* | 4/2008 | Zhou et al. .................... | 436/532 |

OTHER PUBLICATIONS

Murcia, M.J. et al. Biofunctionalization of fluorescent nanoparticles, 2005, Nanotechnologies for the Life Sciences, vol. 1, pp. 1-8.*
Cheng, K.H. et al, Exploration of functionalized CdTe nanoparticles for latent fingerprint detection, Mar. 2008, Journal of Nanoscience and Nanotechnology, vol. 8(3), pp. 1170-1173.*
Menzel, E.R. et al. Functionalized europium oxide nanoparticles for finger print detection: a preliminary study, 2005, Journal of Forensic Identification, vol. 55(2), pp. 189-195.*
Sametband, M., et al., "Application of nanoparticles for the enhancement of latent fingerprints", Chem. Comm., Feb. 19, 2007, pp. 1142-1144, XP00255719, The Royal Society of Chemistry.

(Continued)

*Primary Examiner* — Robert Xu
(74) *Attorney, Agent, or Firm* — Winstead PC

(57) ABSTRACT

Novel conjugates of nanoparticles are provided and have particular utility in the detection of latent fingerprints by their ability to bind to a fingerprint residue. The conjugate comprises a nanoparticle attached to a linker group having a terminal reactive moiety, wherein said nanoparticle comprises a core of a first semiconductor material having a first luminescence and a shell of a second material which at least partially surrounds the core. The conjugated nanoparticle can bind to the fingerprint residue and can be detected using fluorescence.

8 Claims, 10 Drawing Sheets

A

B

C

D

OTHER PUBLICATIONS

Figure 3:
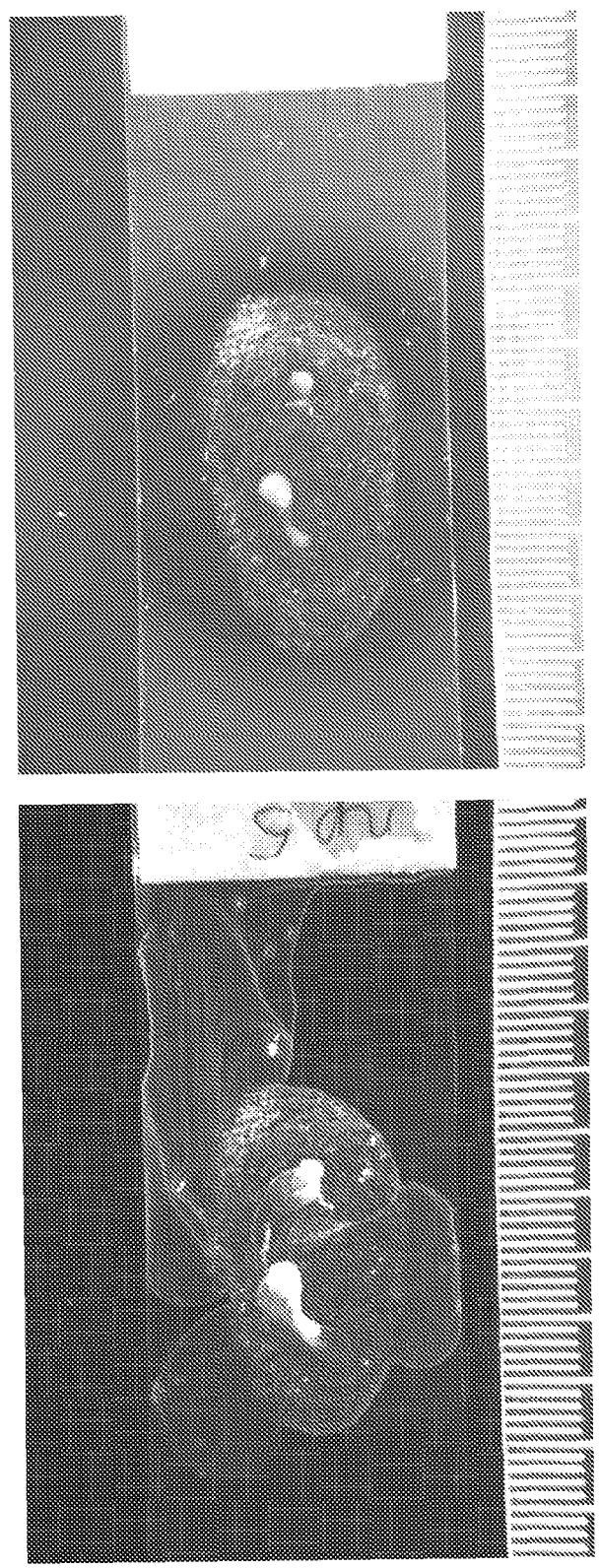

Xie, R., et al., "Colloidal InP Nanocrystals as Efficient Emitters Covering Blue to Near-Infrared", JACS, vo. 129, Nov. 23, 2007, pp. 15432-15433, XP002557200.

Heer, Stephan, "International Search Report", for PCT/GB2009/050699 as mailed Apr. 1, 2010, 6 pages.

Menzel, E. Roland, "Recent Advances in Photoluminescence Detection of Fingerprints", The Scientific World, (2001), 498-509.

Menzel, E. Roland, et al., "Photoluminescent Semiconductor Nanocrystals for Fingerprint Detection", Journal of Forensic Sciences, (2000), 45(3): 545-551.

Menzel, E. Roland, et al., Photoluminescent CdS/Dendrimer Nanocomposites for Fingerprint Detection, Journal of Forensic Sciences, (2000), 45(4): 770-773.

Bouldin, Kimberly K., et al., "Diimide-Enhanced Fingerprint Detection with Photoluminescent CdS/Dendrimer Nanocomposites", Journal of Forensic Sciences, (2000), 45(6): 1239-1242.

Canivez, Y., "Quick and easy measurement of the band gap in semiconductors", Eur. J. PHys. 4 (1983) 42-44.

* cited by examiner

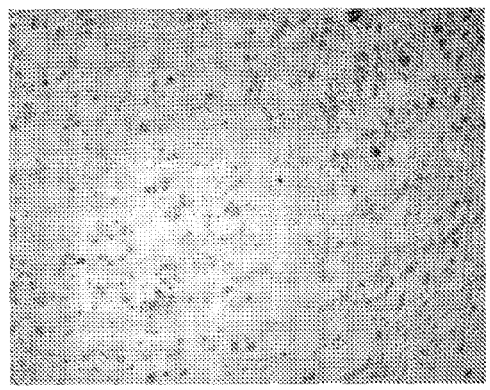 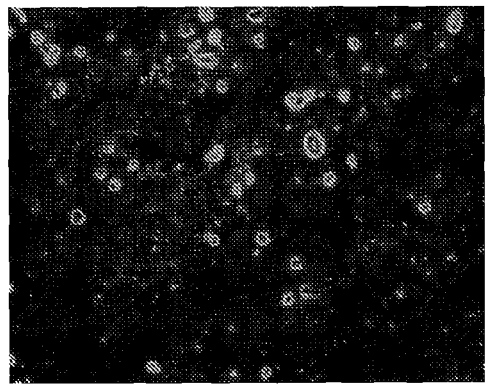
A  B
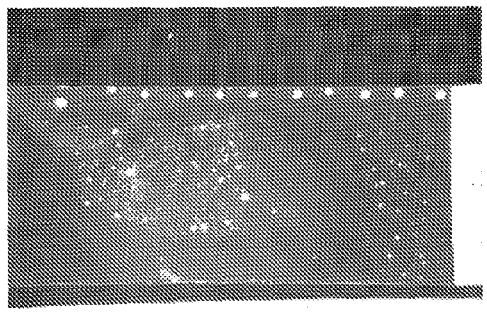 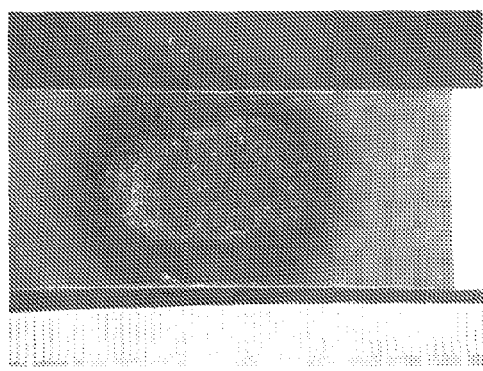
C  D
Fig. 1

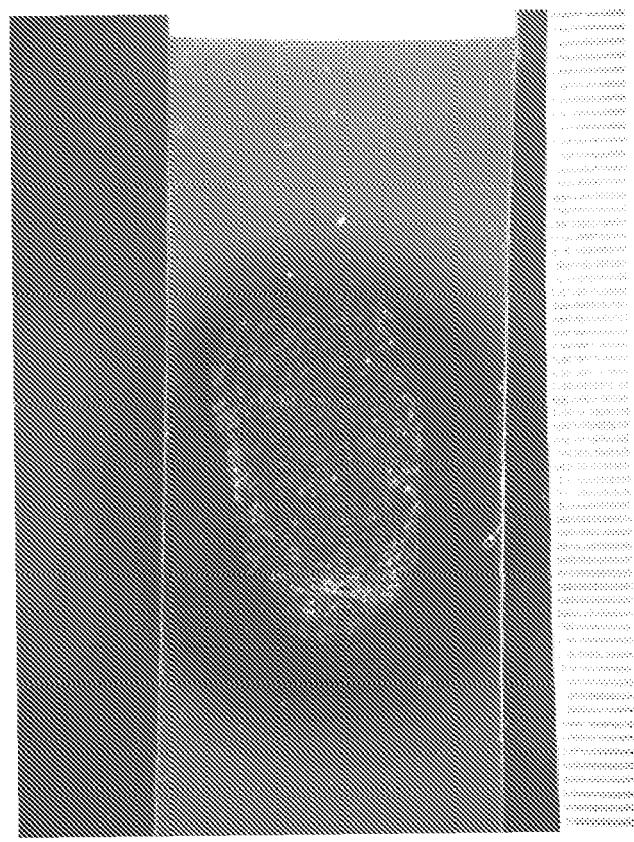
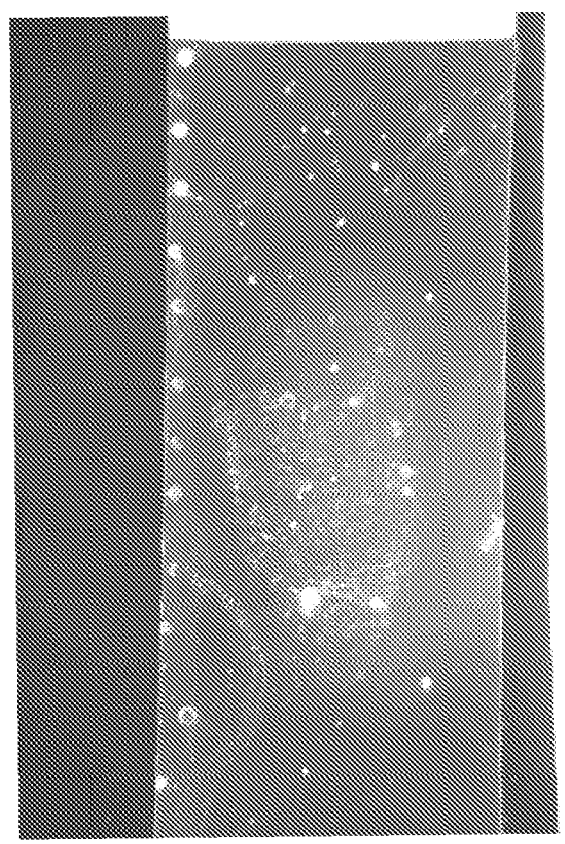
Fig. 2

CONJUGATED NANOPARTICLES AND THEIR USE IN DETECTION OF LATENT FINGERPRINTS

The present invention relates to the use of nanoparticles, in particular cadmium-free nanoparticles, in fingerprint detection and/or visualisation methods.

The detection and/or visualisation of latent fingerprints is an important technique in crime investigation and used routinely by law enforcement agencies in many countries. Latent fingerprints (ie, fingerprints left on an article which cannot be discerned by the naked eye under normal conditions) can be detected using reagents that react with amino acids or other chemicals in the fingerprint residue. The reagents required vary depending upon the surface conditions of the article to be tested. Typical and non exhaustive examples of such conditions may be the porosity or the colour of such surfaces. Typically, ninhydrin or DFO can be used for porous articles, whereas ethyl cyanoacrylate, optionally followed by staining with a fluorescent dye (such as Yellow 40), can be used to test non-porous articles. Different treatments may also be necessary if the article to be treated is wet. Visualization of any fingerprints detected can be enhanced by viewing the treated article under a suitable light source, and the development of photoluminescent techniques has led to an enhancement in fingerprint detection.

Menzel (in The Scientific World, 2001, 1: 498-509) discusses advances in fingerprinting visualisation due to photoluminescence, and in particular the potential use of lanthanides (such as $Eu^{3+}$ and $Tb^{3+}$) to provide luminescent visualisation, and also the use of CdS and CdSe nanoparticles for fingerprint detection.

The use of nanoparticles for fingerprint detection is also discussed in U.S. Pat. No. 6,306,662; Menzel et al., Journal of Forensic Sciences, (2000), 45(3): 545-551 and Menzel et al., Journal of Forensic Sciences, (2000), 45(4): 770-773. CdS is either used in the form of nanocrystals attached to a dioctyl sulfosuccinate label or is attached to a PAMAM dendrimer. Bouldin et al., Journal of Forensic Sciences, (2000), 45(6): 1239-1242, also investigate the use of CdS nanoparticles attached to a PAMAM dendrimer to target fingerprint lipids such as fatty acids or triglycerides.

Sametband et al., Chem Commun, (2007), 1142-1144, compared the use of CdSe/ZnS core-shell nanoparticles to the standard "colloidal gold" on multi-metal-deposition methodology used to visualise latent fingerprints on wet porous surfaces, such as paper or cardboard. The CdSe/ZnS nanoparticles with hydrocarbon chain capping molecules could bind to fingerprint residue by hydrophobic interaction, but background fluorescence for paper prevented this approach being useful in detecting fingerprints on that surface.

Despite the developments in the art noted above, there remains a need for further sensitive techniques for detection and/or visualisation of latent fingerprints. In particular, there is a problem that background colour and/or fluorescence from the article being tested for latent fingerprints can obscure or prevent visualisation of any fingerprints present.

In one aspect, the present invention provides a conjugate comprising a nanoparticle attached to a linker group having a terminal reactive moiety, wherein said nanoparticle comprises a core of a first semiconductor material having a first luminescence, and a shell of a second material which at least partially surrounds the core.

In one embodiment the terminal reactive moiety is a thiocyanate.

In one embodiment the shell comprises two or more layers of the second material, for example 2, 3, 4, 5 or 6 layers. At least one layer will partially surround the core.

In one embodiment the shell can be further covered by one or more different materials.

In one embodiment the first semiconductor material is a fluorescent material, able to produce fluorescence.

The conjugate of core-shell nanoparticles attached to a linker group as discussed herein is of particular utility in detection and/or visualisation of latent fingerprints.

In one embodiment the shell of the nanoparticle is composed of a second material that is different from the first semiconductor material. Optionally, in this embodiment, the shell of the nanoparticle consists of a single layer.

In one embodiment, the shell of the nanoparticle is composed of a second material that is an insulator or a semiconductor with a wider band-gap than that of the first semiconductor material, that is, it absorbs light of a shorter wavelength than the first material. Optionally, in this embodiment, the shell of the nanoparticle consists of a single layer.

The term "band-gap" refers to the energy difference between the top of the valence band and the bottom of the conduction band. A "band-gap" is also known in the art as an "energy gap" or "stop band". Electrons are confined to bands of energy, and can jump from one band to another but are forbidden from other regions. The conductivity of semiconductor materials is dependent upon the band-gap since only the electrons with sufficient thermal energy to be excited across the band-gap and can act as conductors. Band-gap can be altered by controlling the composition of semiconductor composite materials. Since band-gap values also depend upon temperature and pressure, band-gap values referenced herein refer to band-gap at 300K and atmospheric pressure.

Suitable techniques for measurement of band-gaps are available in the art, but mention can be made of (Canivez Eur J. Phys 4:42-44 (1983).

The core of the nanoparticle is formed from a semiconductor material which can be of any fluorescent material which is non-toxic. Suitable materials include semiconductors containing one or more of the elements Al, Ga, In, Zn, N, P, or S. The semiconductor material can be binary (examples include AlN, AlP, GaN, GaP, InN, InP or ZnS; preferably GaN, GaP, InN or InP; and more preferably InP), ternary (for example $M_xM'_{1-x}E$ or $ME_yE'_{1-y}$, where M and M' are each independently Al, Ga or In; E and E' are each independently N or P, x and y are each independently 0 or 1), or quaternary (for example of formula $M_xM'_{1-x}E_yE'_{1-y}$ where M, M', E, E', x and y are as defined above).

In one embodiment, the first semiconductor material of the core is selected so that the colour of its fluorescence emission can be tuned within the visible region of the spectrum by varying the diameter of the core. Thus, the diameter size of the core of the nanoparticles can be selected so that the light emitted from it is of a different (and preferably contrasting) colour from any background fluorescence emitted from the article on which the fingerprint residue is located. This ability to change the colour of the core has the advantage of enabling selection of a suitable contrast between the nanoparticle attached to the fingerprint residue and the article. Preferred core diameter sizes are from 0.5 to 20 nm, more preferably from 1 to 10 nm.

The shell of the nanoparticles can also consist of a semiconductor, which is formed from a second semiconductor material. In such case, suitable materials for the second material include a compound semiconductor containing one or more elements from the following list: Al, Ga, In, Zn, N, P or S. A preferred example is ZnS or ZnO. When it is a semiconductor, the second material is preferably selected so that its band-gap is wider than that of the first semiconductor material.

The thickness of the shell is selected to be sufficient to confine the hole-electron pair generated by excitation of the first semiconductor material within the core. Suitable shell thicknesses are from 0.1 to 10 nm, more preferably from 0.2 to 2 nm.

Suitable nanoparticles are available from Nanoco Technologies Ltd (Manchester, UK) and are described in the literature (e.g. Peng et al., Journal of The American Chemical Society, (2007), 129, 15432). Particular mention can be made of Cadmium Free Quantum Dots (CFQD Green) having a nominal emission of 521 nm and a nominal FWHM of 61 nm.

In the invention, the nanoparticles are attached to one or more linker groups to form a conjugate.

In one embodiment, the linker group is provided from a compound of formula I

$$A(R_1\text{---}B)_n \qquad I$$

wherein A and B are each functional groups, and may be the same or different;
$R_1$ is a saturated or unsaturated $C_{1-50}$ hydrocarbon chain, optionally interrupted by one or more of —O—, —S—, —NH—, or —$NR_x$— groups, where $R_x$ is a saturated or unsaturated $C_{1-20}$ alkyl chain, optionally containing O, S, NH or NR, where group R is as defined below; and n is 1, 2, or 3.

Where n is 2 or 3, each $R_1$ group and/or each B group can be independently selected.

In some embodiments, $R_1$ is a saturated or unsaturated $C_{1-24}$ hydrocarbon chain, more preferably a $C_6$-$C_{18}$ preferably a $C_4$-$C_{24}$ hydrocarbon chain, more preferably a $C_6$-$C_{18}$ or $C_8$-$C_{14}$ (for example $C_8$, $C_9$, $C_{10}$, $C_{11}$, $C_{12}$, $C_{13}$ or $C_{14}$) hydrocarbon chain. Where $R_1$ is unsaturated it can comprise 1, 2, 3 or more double or triple bonds.

Group A can be any functional group which can attach either to the fingerprint residue or to the nanoparticle, preferably to the nanoparticle. Non-limiting examples can be selected from P=S, P=O, P, or N in which case n=3; O, S, RP, NR, RP=O, RP=S where R is a $C_{1-20}$ alkyl chain, optionally containing O, S, NH, NR, and/or optionally containing one or more double or triple bonds, in which case n=2; or $CO_2H$, CHO, SH, $NH_2$, $NR_2$, NHR, $PR_2$, O=$PR_2$, S=$PR_2$, $CO_2R$, OCN, SCN, NCS, NCO, where R is as defined above, in which case n=1. In one embodiment, group A binds to the nanoparticle to form a conjugate of formula II:

$$Q\text{-}A^2(R_1\text{---}B)_m \qquad II$$

where Q is a nanoparticle (and in particular is a nanoparticle as described above); and
$R_1$ is as defined above;
B is as defined above; and
m is 1 and $A^2$ is —O—, —S—, —C(=O)—, —O—C(=O), —C(=O)—O—, —NH—, —NR—, —P(=O)—, —P(=S)—, —P(=O)($R_2$)—, —P(=S)($R_2$)—, —P($R_2$)$_2$ or —P($R_2$)$_3$, where each $R_2$ is independently selected from OH, OR or R; or
m is 2 and $A^2$ is N, P=O, P=S, P($R_2$) or P($R_2$)$_2$; or
m is 3 and $A^2$ is —O=P, —S=P, —P, —P($R_2$);
where R is as defined above.

In certain embodiments the linker can be attached to the nanoparticle by a dative covalent bond, for example through a phosphorus, through the oxygen of a —O=P group (or sulphur of a —S=P group) where the phosphorus is bound to up to 3 ($R_1$—B) groups (which can each be the same or different).

Group B can be any functional group which can attach to the nanoparticle or to the fingerprint residue, preferably to the fingerprint residue. Non-exclusive examples include: —$CO_2H$, CHO, SH, $NH_2$, $NR_2$, NHR, $PR_2$, O=$PR_2$, S=$PR_2$, $CO_2R$, OCN, SCN, NCS, NCO, where R is as defined above for group $A^2$. More preferred examples include SH, $NH_2NR_2$, NHR, $PR_2$, O=$PR_2$, S=$PR_2$, OCN, SCN, NCS or NCO, where R is as defined above for group $A^2$. In one embodiment, group B is the reactive moiety able to bind to a fingerprint residue.

Where n=1, $A^2$ and B can be the same or different. $R_1$ can be a $C_{1-50}$ hydrocarbon chain (preferably a $C_{1-24}$ hydrocarbon chain) in which any of the carbon atoms can be optionally replaced by O, S, NH, $NR_x$ (where $R_x$ is as defined above), and/or optionally containing 1 or more double or triple bonds. In the cases where n=2 or 3, each group $R_1$ can be the same or different.

In one embodiment, $A^2$ is attached to the nanoparticle, n is 1, group $R_1$ is a saturated $C_6$-$C_{24}$ (preferably $C_7$, $C_7$, $C_8$, $C_9$, $C_{10}$, $C_{11}$, $C_{12}$, $C_{13}$ or $C_{14}$) alkyl group or is an unsaturated $C_6$-$C_{24}$ (preferably $C_6$, $C_7$, $C_8$, $C_9$, $C_{10}$, $C_{11}$, $C_{12}$, $C_{13}$ or $C_{14}$) alkyl group having one double bond and group B is NCS, NCO, SCN or OCN (preferably NCS or NCO, more preferably NCS). Optionally, in this embodiment, $A^2$ is a carboxylate group.

In one embodiment, groups $A^2$ and B are selected so that the conjugate is able to react rapidly within a timescale of 5-30 seconds with the fingerprint residue under mild conditions, that is either room temperature or gentle heat with a hairdryer for a time periods of 5-30 seconds and without requiring other chemicals.

In one embodiment, $A^2$ and/or B is —NCS.

In one embodiment, more than one type of linker group is attached to the nanoparticle and this can be advantageous by providing a spectrum of reactivity on the conjugate. For other embodiments, a single type of linker moiety may be advantageous to provide an increased level of reactivity to the target reactants on the fingerprint residue.

In one embodiment, the linker group(s) is selected so that the conjugate is soluble in a solvent. Conveniently the solvent is suitable for application to the articles to be tested and allows attachment of the conjugate to the fingerprint residue.

The linker groups can be introduced onto the surface of the nanoparticle during the synthesis of the nanoparticles; it can displace a molecule such as a surfactant that has been introduced during the growth process; or it can be synthesized by some form of chemistry between a molecule introduced onto the particle during growth and some other agent. The linker group can also be introduced onto the surface by any combination of the aforementioned techniques. These methods are shown schematically in Scheme 1.

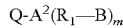

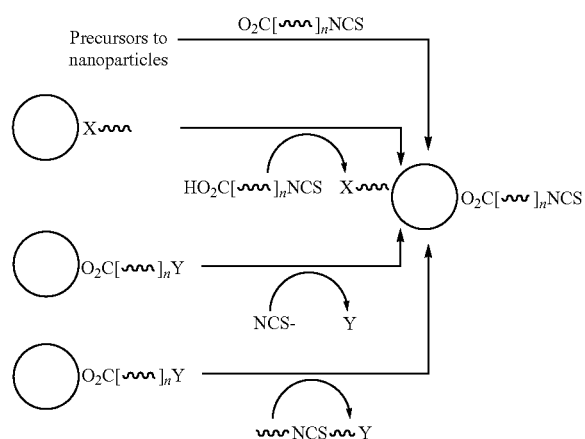

Scheme 1. Methods for introducing a typical linker group onto the nanoparticle, depicted by the circle. Only one initial capping group and one linker group are shown, for simplicity. X is any group attached to the nanoparticle; Y is any functional group displaceable by thiocyanate; and n indicates that the hydrocarbon chain (which may typically be saturated or unsaturated and can include other heteroatoms) has from 1 to 50 carbon atoms in its backbone as discussed above. In the first option, the nanoparticle is produced and the linker attached in a one-stage process. In the second option, a pre-linked nanoparticle is modified by swapping out the previous linker group for the linker group according to the invention. In the third option, the hydrocarbon spacer group of an existing linker group is extended and the terminal functionality changed. In the fourth option, the terminal functionality of an existing linker group is changed, here to a thiocyanate.

In one embodiment, a capped nanoparticle can undergo ligand exchange to produce a conjugate according to the invention. The capped nanoparticle starting material can be exposed to a 10-20 fold excess of a ligand of formula I for a suitable period of time (24 to 72 hours is usually sufficient), at room temperature or optionally with mild heating.

The present invention also provides a method of producing a conjugate as described above, said method comprising exposing a core-shell nanoparticle formed of first and second semiconductor materials to a compound of formula I:

$$A(R_1-B)_n \qquad \text{I}$$

wherein A, $R_1$, B and n are as defined above for the linker group, and allowing the nanoparticle and linker group to react together to form a conjugate of formula II.

In one embodiment group A is a carboxylate group and attaches covalently to the metal atom on the surface of the nanoparticle.

In one embodiment group A is attached to the nanoparticle, $R_1$ is a $C_{6-24}$ saturated or unsaturated hydrocarbon chain and group B is isothiocyanate and n can be 1, 2, or 3. In one embodiment group A can be COOH, n is 1, and B is isothiocyanate.

The present invention further provides a method of detecting latent fingerprints, said method comprising attaching core-shell nanoparticles (preferably in the form of a conjugate of formula II) as described above to a fingerprint residue and detecting the fingerprint. The latent fingerprint will generally be present as a fingerprint residue left on an article and the nanoparticles (usually in the form of a conjugate) will be applied to the article.

The term "fingerprint residue" refers to the material left behind on an article when touched by a finger or thumb. The fingerprint residue will normally comprise lipid (eg fatty acid or triglyceride) components and/or amino components.

In one embodiment, the step of detecting the fingerprint comprises visualising the nanoparticles (usually in the form of a conjugate as described above) attached to the fingerprint residue by optical means including, but not limited to, fluorescence. Ultraviolet (UV) and monochromatic or wide spectral bandwidth (e.g. white light) sources can be used, alone or in combination. Conveniently, the fingerprint image is captured by photography.

In one embodiment, the nanoparticles are in the form of a conjugate attached to linker group(s) as described above. Conveniently, the linker groups are selected to be suitable for reaction to the fingerprint residue and non-reactivity to the article per se.

The modified nanoparticles can be introduced to the fingerprint residue as a solution (or suspension) in a solvent or as a dry powder. Suitable solvents include any solvent that will disperse the nanoparticles. Non-limiting examples of the solvent include: a hydrocarbon, an aromatic solvent, an ether, a ketone, a chlorinated solvent, a polar aprotic solvent, an alcohol, water or a combination of such solvents. Preferably the solvent is of very low toxicity. Preferred solvents include toluene, acetone or water.

If introduced in a solvent, the nanoparticle solution (or suspension) can be applied to the substrate bearing the fingerprint residue in any manner suitable. Non-limiting examples of application methods include: spraying, dripping, spin coating, or dipping the substrate into the solution. A preferred method is spraying.

Optionally, the article can be washed with the solvent, or other suitable solvent to remove excess conjugate and/or nanoparticles. A washing step can improve discernment of fingerprint ridge detail.

The applied solution can be allowed to react at room temperature or can be heated gently e.g. with a hair-drier. The washing step, if conducted, can conveniently take place prior to or after the drying step.

The present invention will now be further described with reference to the following, non-limiting, examples and figures, in which:

FIG. 1 Micrographs: diascopic, magnification=40× (a), epifluorescence, magnification=100× (b), photographs: fluorescence under UV excitation (c), white light scattering (d) showing an oily fingerprint residue sprayed with a toluene solution of nanoparticles on glass.

FIG. 2 Photographs: fluorescence under UV excitation (a), white light scattering (b) showing an oily fingerprint residue on glass which has been sprayed with a toluene solution of nanoparticles, washed with neat toluene and dried.

FIG. 3 Photographs: fluorescence under UV excitation (a), white light scattering (b) showing an oily fingerprint residue on glass which has been drip coated with a toluene solution of nanoparticles.

Figure 4:
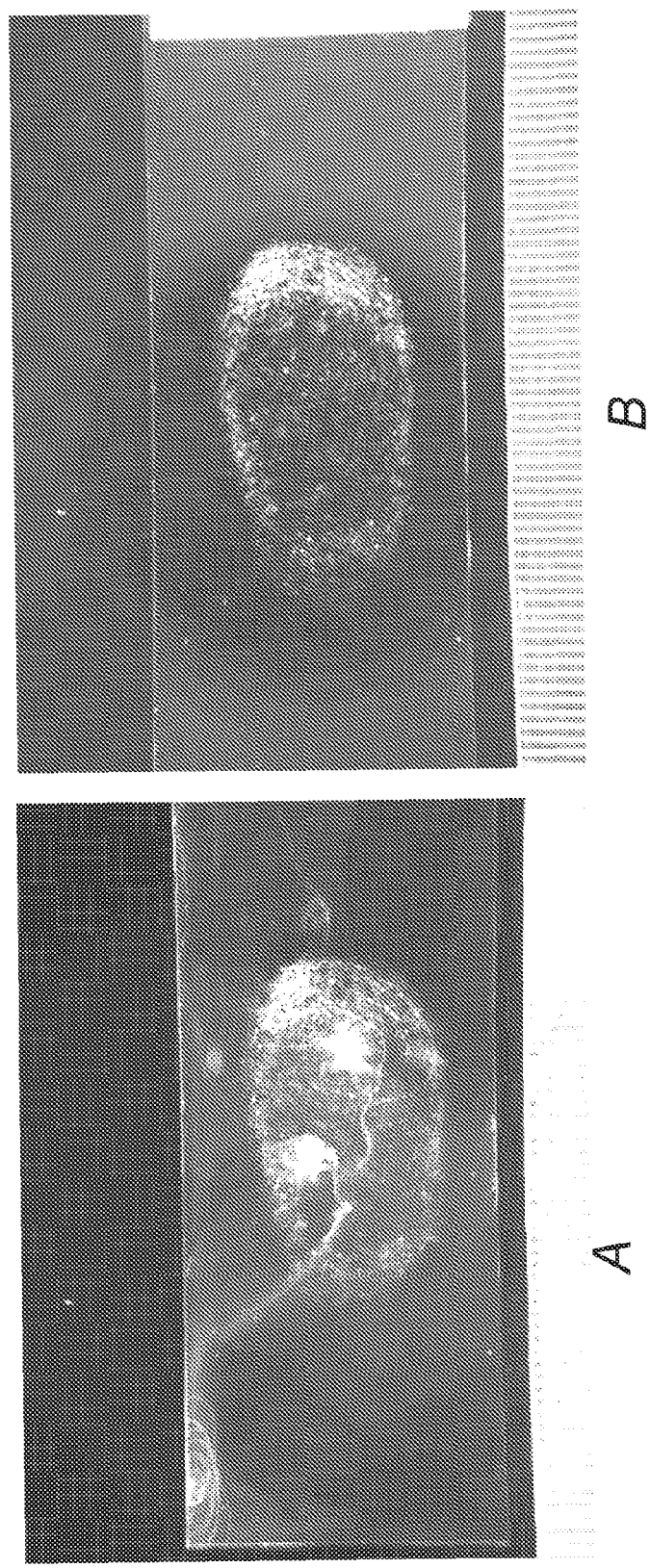

FIG. 4 Photographs: fluorescence under UV excitation (a), white light scattering (b) showing an oily fingerprint residue on glass which has been drip coated with a toluene solution of nanoparticles, washed with neat toluene and dried.

Figure 5:
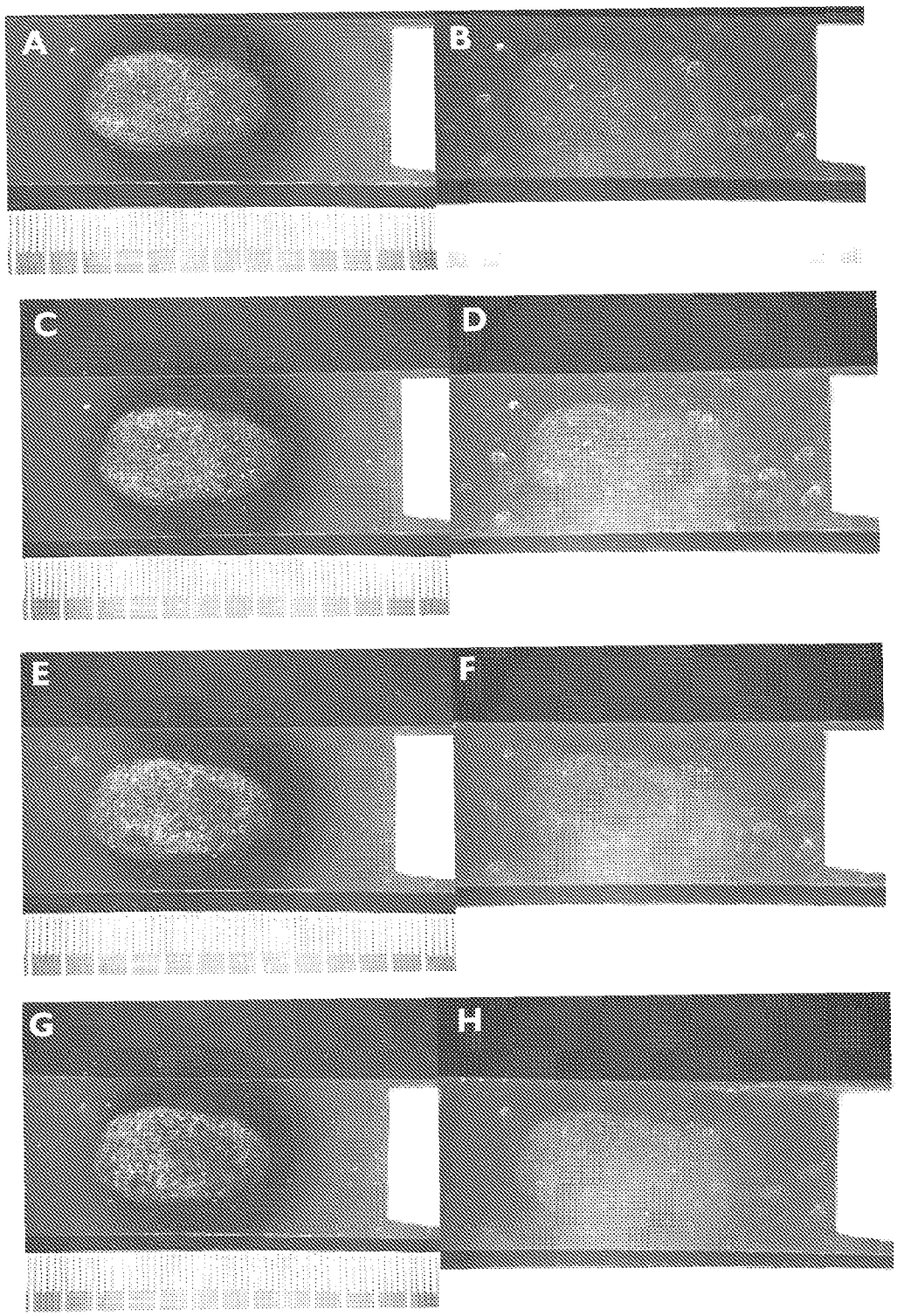

FIG. 5. Photographs showing an oily fingerprint on glass which has been sprayed ×8 with a toluene solution of nanoparticles and dried. (a) No washing, white light mode and (b) UV mode, (c) washed ×1 with neat toluene, white light mode and (d) UV mode, (e) washed ×5 with neat toluene, white light mode and (f) UV mode, (g) washed ×13 with neat toluene, white light mode and (h) UV mode. After each washing the sample was dried.

Figure 6:
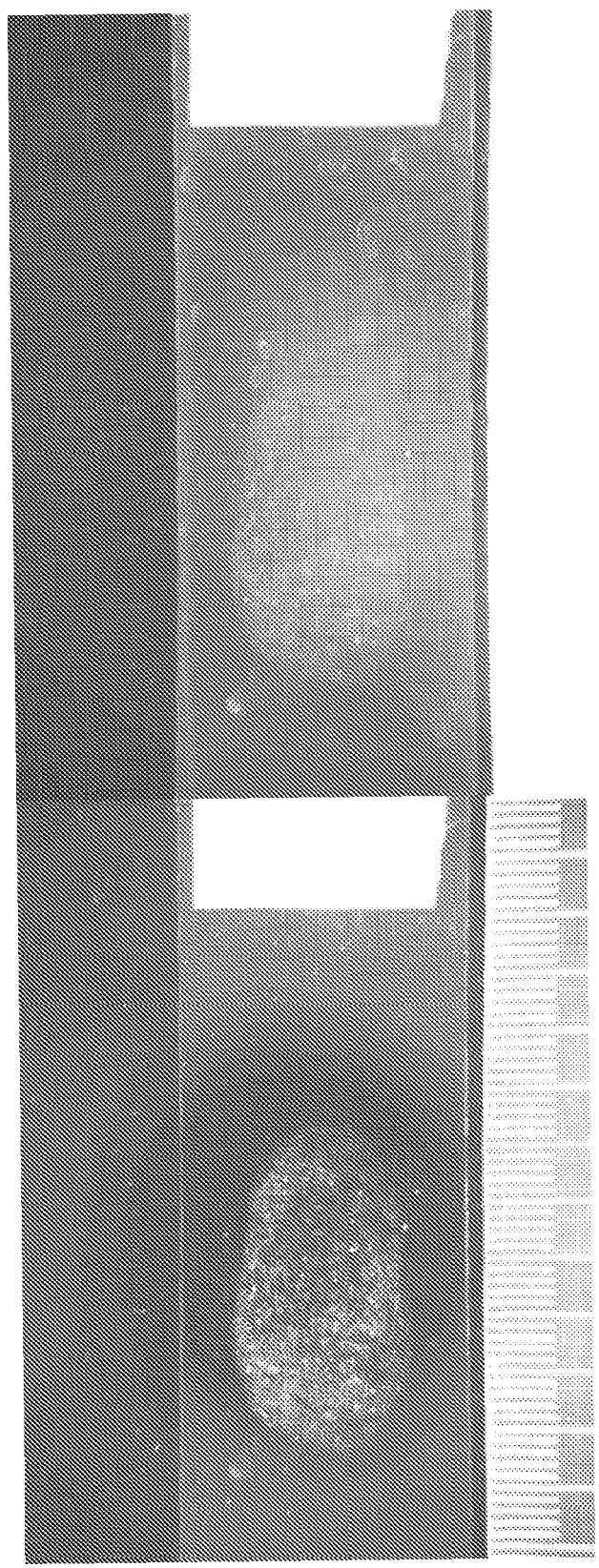

FIG. 6. Photographs showing an oily fingerprint on glass which has been sprayed ×8 with a toluene solution of unmodified nanoparticles and dried. The sample was washed by dipping the glass into neat toluene (a) white light mode and (b) UV mode.

Figure 7:
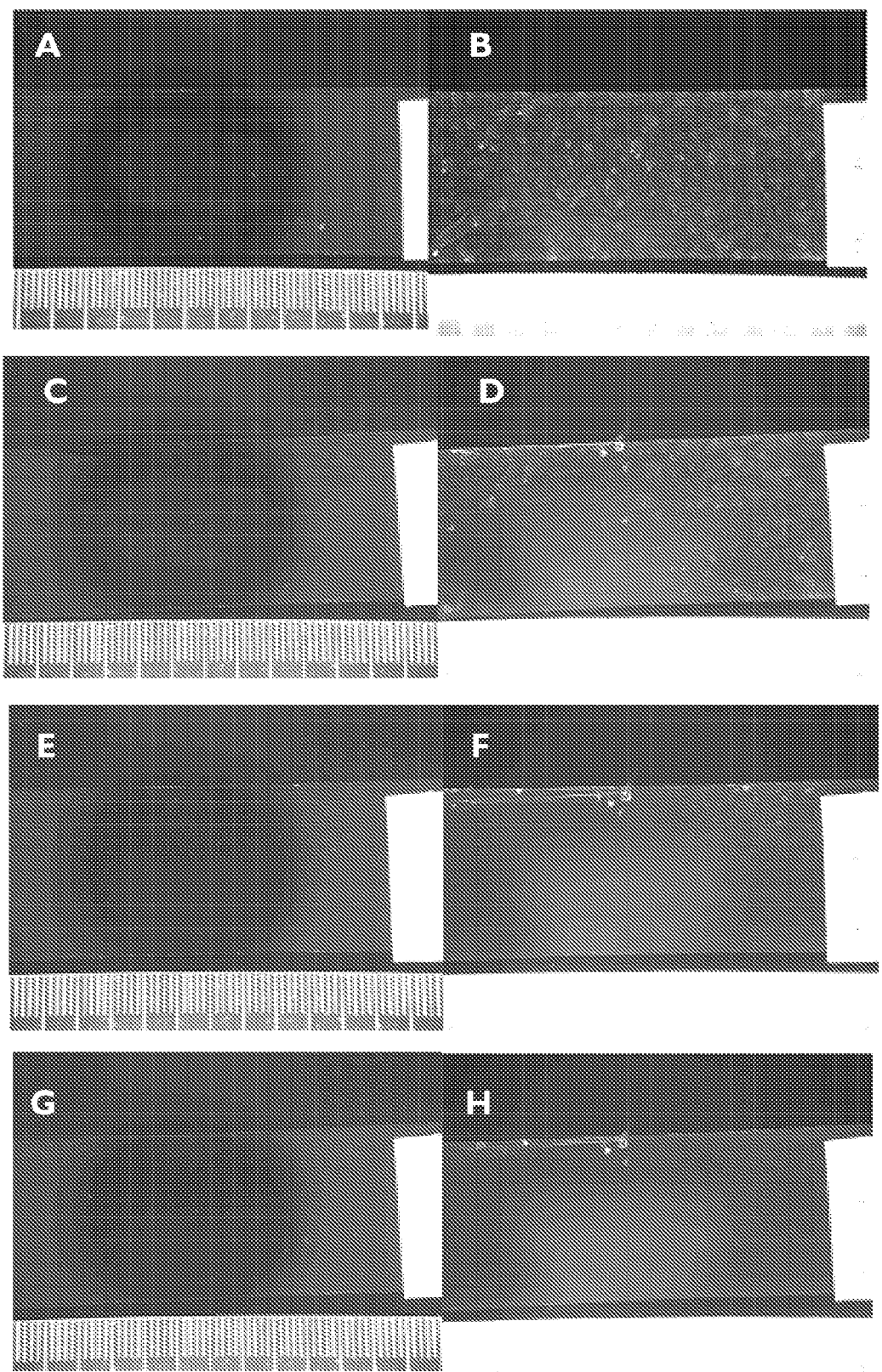

FIG. 7. Photographs showing an oily fingerprint on glass sprayed with unmodified nanoparticles. (a) No washing, white light mode and (b) UV mode, (c) washed ×1 with neat toluene, white light mode and (d) UV mode, (e) washed ×4 with neat toluene, white light mode and (f) UV mode, (g) washed ×8 with neat toluene, white light mode and (h) UV mode. After each washing the sample was dried.

Figure 8:
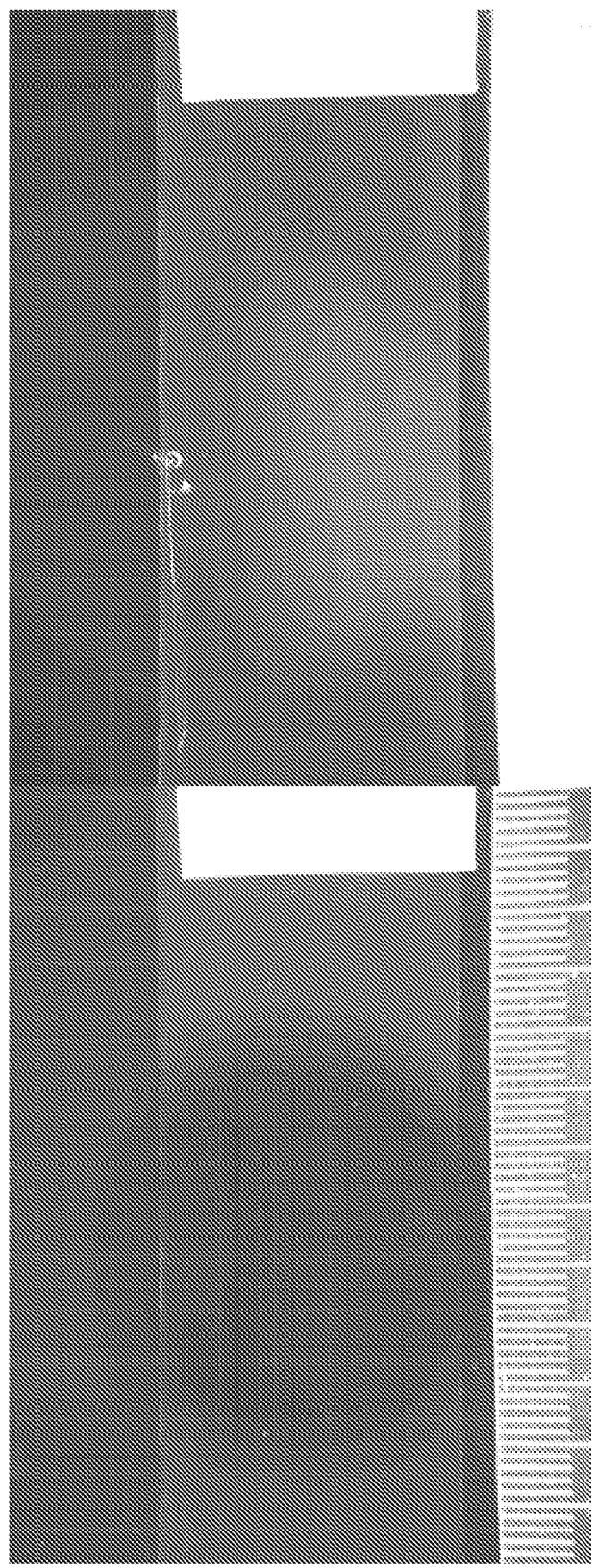

FIG. 8. Photographs showing an oily fingerprint on glass which has been sprayed ×8 with a toluene solution of unmodified nanoparticles and dried. The sample was washed by dipping the glass into neat toluene (a) white light mode and (b) UV mode.

Figure 9:
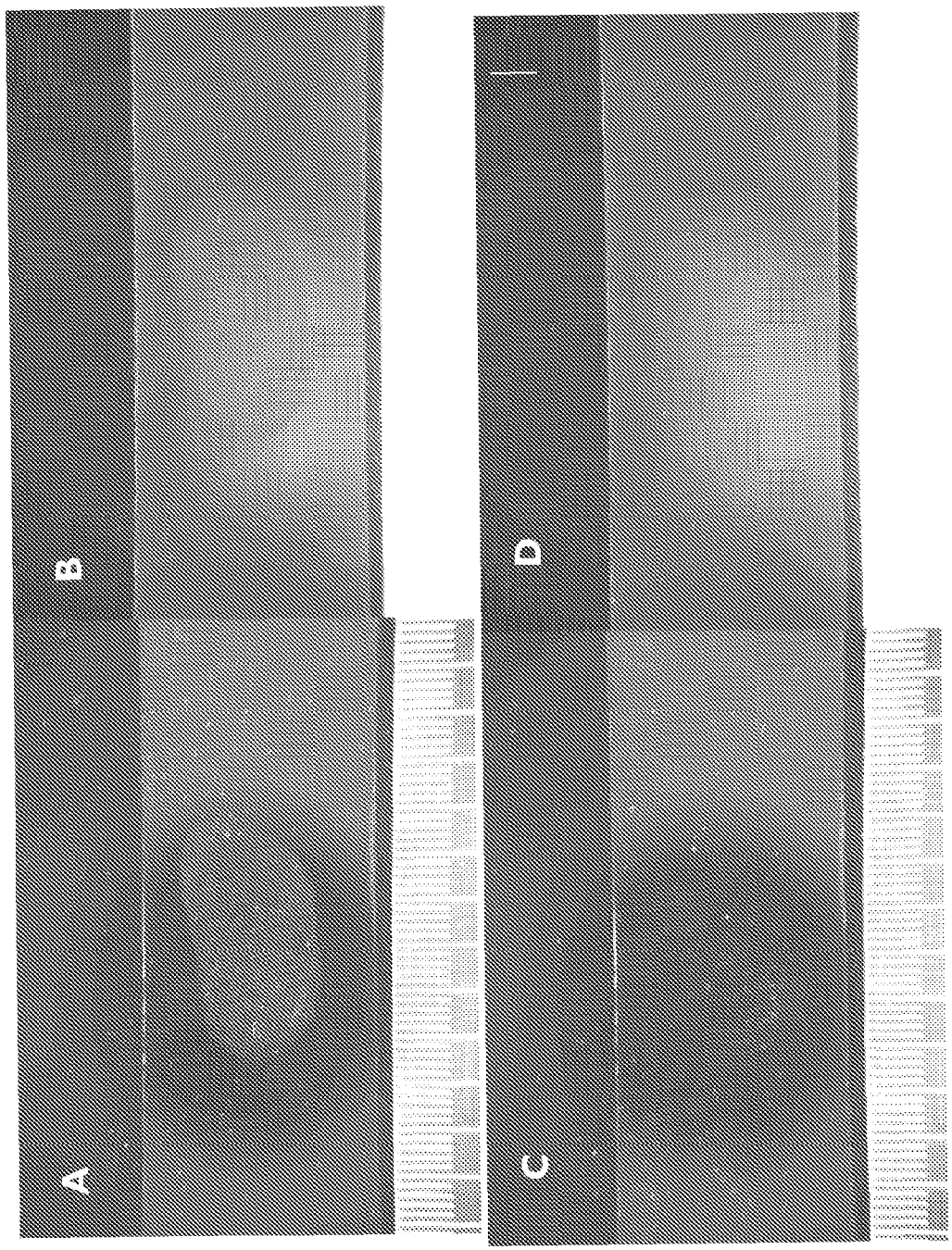

FIG. 9. Photographs showing an oily fingerprint on glass (a) white light mode and (b) UV mode. The fingerprint was washed from the glass by neat toluene (c) white light mode and (d) UV mode.

Figure 10:
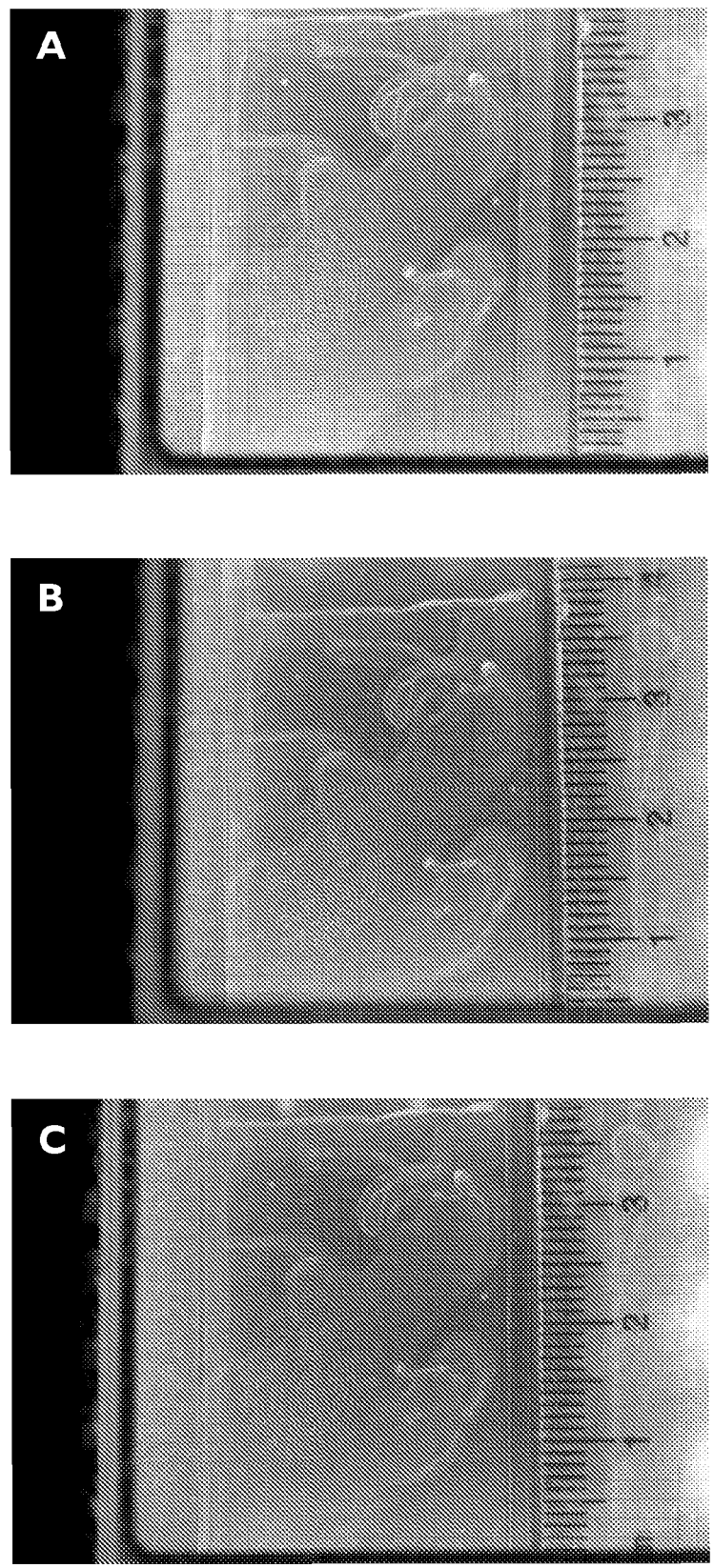

FIG. 10. Photographs showing an oily fingerprint drip coated with a toluene solution of modified nanoparticles on glass. (a) Dried and ×1 neat toluene wash, (b) ×3 wash and (c) ×6 wash.

In Examples 1 to 4 described below, the samples were examined using one of the following:

1. An Olympus (model, CKX41) optical microscope fitted with an Olympus epifluorescence attachment, U-RFLT50. The samples were viewed separately in both diascopic (transmitted light) and epifluorescence (fluorescence by incident excitation) modes. All diascopic/fluorescence micrographs were taken with either an ×4 objective (numeric aperture 0.13) or ×10 objective (numeric aperture 0.25) The micrographs were recorded using a Nikon (model, Coolpix 950) digital camera attached to the microscope.
2. A Syngene (model, GeneFlash) gel documentation system fitted with a CCD camera. The samples were viewed separately in both UV (fluorescence) and white light (scattering) modes. All photographs were taken at one of the following exposure times: 0.12 s, 0.32 s, 0.48 s, 0.72 s, 1.00 s.

EXAMPLE 1

Preparation of the Conjugate; Core-Shell Nanoparticles Attached to a Linker Group The preparation involves the following synthetic steps:
1. Synthesis of 12-Isothiocyanatododecanoic Acid

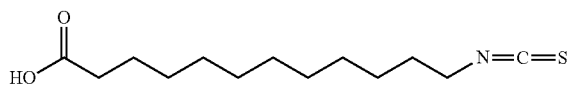 [SMILES: O=C(O)CCCCCCCCCCCN=C=S]

Solvents were dried and degassed by standard methods unless otherwise stated. Chemicals were obtained from Aldrich, UK (reagent grade) and were used as received unless otherwise stated. Reactions were carried out under a nitrogen atmosphere using standard Schlenk line techniques.

An aqueous solution (200 mL) of $K_2CO_3$ (1.97 g) was added dropwise during 1 hour to a well-mixed suspension of 12-aminooctanoic acid (4 g, 18.58 mmol) and thiophosgene (1.4 ml, 18.58 mmol) in dichloromethane (160 ml). The reaction mixture was stirred for 2 hours at room temperature. The organic layer was then separated and the water layer extracted with dichloromethane (3×15 mL). The combined organic fractions were collected and dried over $MgSO_4$. After filtration, the solution was evaporated in vacuo leaving behind a yellow waxy solid (approximately 3 g). The crude product was dissolved in dichloromethane (100 mL) and stirred for approximately 2 minutes. The resulting suspension was filtered under gravity giving a clear yellow filtrate which was evaporated to yield yellow oil. Yield: 75%. IR (nujol mull, $cm^{-1}$): 2190, 2086 (NCS), 1713 (C=O). $^1$H NMR ($CDCl_3$, ppm): δ 1.20-1.40 (m, 14H, $(CH_2)_7$), 1.59 (m, 4H, $(CH_2)_2$), 2.28 (t, 2H, $CH_2$—COOH), 3.44 (t, 2H, $CH_2$—NCS). $^{13}$C NMR ($CDCl_3$, ppm): δ 24.67, 26.56, 28.79, 29.04, 29.21, 29.35, 29.41, 29.97, 34.05, 45.08, 129.05 (NCS), 180.06 (COOH). Anal. calculated for $C_{13}H_{23}NO_2S$ ( ): C, 60.66; H, 9.01; N, 5.44. Found: C, 58.48; H, 8.45; N, 5.33. TOF: m/z (%) 280 ($[M+Na]^+$, 100). m/z 280.1342 calc 280.1347, Δ=−1.8 ppm.

2. Exchange of Surface Myristic Acid for 12-Isothiocyanatododecanoic Acid

Solvents were dried and degassed by standard methods unless otherwise stated. Chemicals were obtained from Aldrich, UK (reagent grade) and were used as received unless otherwise stated. Reactions were carried out under a nitrogen atmosphere using standard Schlenk line techniques. A toluene solution (5 ml) of 12-isothiocyanatododecanoic acid was added to a toluene solution (0.25 ml) of InP/ZnS/myristic acid nanoparticles (approximately 20 mg). After stirring at room temperature for 16 hours, the nanoparticles were precipitated using methanol in a ratio of 1:4, collected by centrifuging at 6,000 rpm for 15 minutes and then dried under nitrogen. The nanoparticles were redissolved up in toluene (5 ml). The precipitated nanoparticles were characterized by IR (KBr disk, $cm^{-1}$): 2179, 2099 (NCS).

3. Loading of the Nanoparticles onto the Article Bearing the Fingerprint Residue The article bearing the fingerprint residue was a glass microscope slide. Preparation of the microscope slides were carried out as follows. A finger whose surface is covered by its natural sebaceous layer was pressed down onto one side of the microscope slide surface leaving behind an oily fingerprint residue. A toluene solution (suspension) of prepared fluorescent nanoparticles (from step 2 above) was sprayed four times onto the same surface of the microscope slide and left to partially air dry. Thereafter, the same surface was gently heated using a hairdryer for approximately 20 seconds to complete the drying procedure. The fingerprint on the microscope slide was imaged separately at this stage in both white light scattering and UV fluorescence modes. Two different instruments were used; an Olympus microscope and a Syngene GeneFlash cabinet. Images are shown in FIG. 1.

EXAMPLE 2

As example 1 but, after imaging, the excess nanoparticle solution was removed by washing with five sprays of neat toluene. The same drying procedure (Example 1) was applied. The fingerprint on the microscope slide was imaged separately at this stage in both white light scattering and UV fluorescence modes using a Syngene GeneFlash cabinet. The images are shown in FIG. 2.

EXAMPLE 3

A finger whose surface is covered by its natural sebaceous layer was pressed down onto one side of the microscope slide surface leaving behind an oily fingerprint residue. A toluene solution (suspension) of prepared nanoparticles was taken up into a glass pipette and three large drops were directly placed onto the fingerprint. The microscope slide was carefully maneuvered in order for the nanoparticle solution to completely cover the fingerprint residue. The solution on the slide was left to partially air dry and then gently heated using a hairdryer for approximately 20 seconds to complete the drying procedure. The fingerprint on the microscope slide was imaged separately at this stage in both white light scattering and UV fluorescence modes using a Syngene GeneFlash cabinet. The images are shown in FIG. 3.

EXAMPLE 4

As Example 3, but after imaging, the excess nanoparticle solution was removed by washing with five sprays of neat toluene. The same drying procedure (Example 1) was applied. The fingerprint on the microscope slide was imaged separately at this stage in both white light scattering and UV fluorescence modes using a Syngene GeneFlash cabinet. The images are shown in FIG. 4.

In Examples 5 to 13 described below, the samples were examined using either:

1. A Syngene (model, GeneFlash) gel documentation system fitted with a CCD camera. The samples were viewed separately in both UV and white light (transmission) modes. All photographs were taken at one of the following exposure times: 0.12 s, 0.32 s, 0.48 s, 0.72 s, 1.00 s.
2. A LED light source, composed of multiple LED's whose central wavelength of the emission peak, which is 80 nm broad, is 450 nm. Under such illumination, the sample is imaged using a commercial digital camera (Fujifilm FinePix S5 Pro). Interposing between camera and sample, a filter (either 495 nm long pass or 550 nm long pass) that blocks the illumination wavelength, and that allows the fluorescence excited by the illumination to pass through and reach the camera.
3. An Olympus (model, CKX41) optical microscope fitted with an Olympus epi fluorescence attachment, U-RFLT50. The samples were viewed separately in both optical (reflectance) and fluorescence (transmission) modes. All optical/fluorescence micrographs were taken with either an ×40 objective (numeric aperture 0.13) or ×100 objective (numeric aperture 0.25). The micrographs were recorded using a Nikon (model, Coolpix 950) digital camera attached to the microscope.

EXAMPLE 5

The procedure of Example 2 was followed except that the nanoparticle solution was sprayed onto the microscope slide containing the fingerprint 8 times rather than 4. The sample was then dried (as described in Example 1) and thereafter, washed by spraying neat toluene ×1, ×5 and ×13, respectively. The sample was dried between each wash (FIG. 5).

EXAMPLE 6

The procedure of Example 5 was followed except that the microscope slide containing the nanoparticle tagged fingerprint was washed by dipping into a full beaker of neat toluene. The results are shown in FIG. 6.

EXAMPLE 7

Comparative Example

The substrate bearing the fingerprints was a glass microscope slide. Preparation of the microscope slides were carried out as follows. An oily finger was pressed down hard onto one side of the microscope slide surface leaving behind an oily fingerprint. A toluene solution (suspension) of as received CFQD from Nanoco (i.e. unmodified nanoparticles) was prepared. The diluted solution was sprayed eight times onto the same surface of the microscope slide and left to partially air dry. Thereafter, the same surface was gently heated using a hairdryer for approximately 20 seconds to complete the drying procedure. The fingerprint on the microscope slide was imaged separately at this stage in both white light and UV light (FIGS. 7(a) and (b)). Thereafter, the sample was washed by spraying neat toluene ×1, ×4 and ×8, respectively. The sample was dried between each wash (FIG. 7(c)-(h)).

EXAMPLE 8

Comparative Example

The procedure of Example 7 was followed except that the microscope slide containing the unmodified nanoparticles and fingerprint was washed by dipping into a full beaker of neat toluene. The results are shown in FIG. 8.

EXAMPLE 9

Comparative Example

The substrate bearing the fingerprints was a glass microscope slide. An oily finger was pressed down hard onto one side of the microscope slide surface leaving behind an oily fingerprint. The sample was washed by spraying neat toluene eight times. The fingerprint on the microscope slide was imaged separately in both white light and UV light (FIG. 9).

EXAMPLE 10

An oily finger was pressed down onto one side of the microscope slide surface leaving behind an oily fingerprint. A dichloromethane solution (suspension) of modified nanoparticles was taken up into a glass pipette and three large drops were directly placed onto the fingerprint. The microscope slide was carefully maneuvered in order for the nanoparticle solution to completely cover the fingerprint. The solution on the slide was left to partially air dry and then gently heated using a hairdryer for approximately 20 seconds to complete the drying procedure. The fingerprint on the microscope slide was imaged using the LED light source. In the middle of a microscope slide, an image of a fingerprint could be seen. Both the outline and fingerprint ridge detail were shown. The image appeared fluorescent yellow due to the yellow modified nanoparticles binding to the fingerprint residue. Also, a few fluorescent yellow spots appeared over some areas of the microscope slide near to the fingerprint where the solution of nanoparticles was allowed to run off the slide.

EXAMPLE 11

Cross Metathesis of Vinyl-Terminated Nanoparticle Surface Ligands

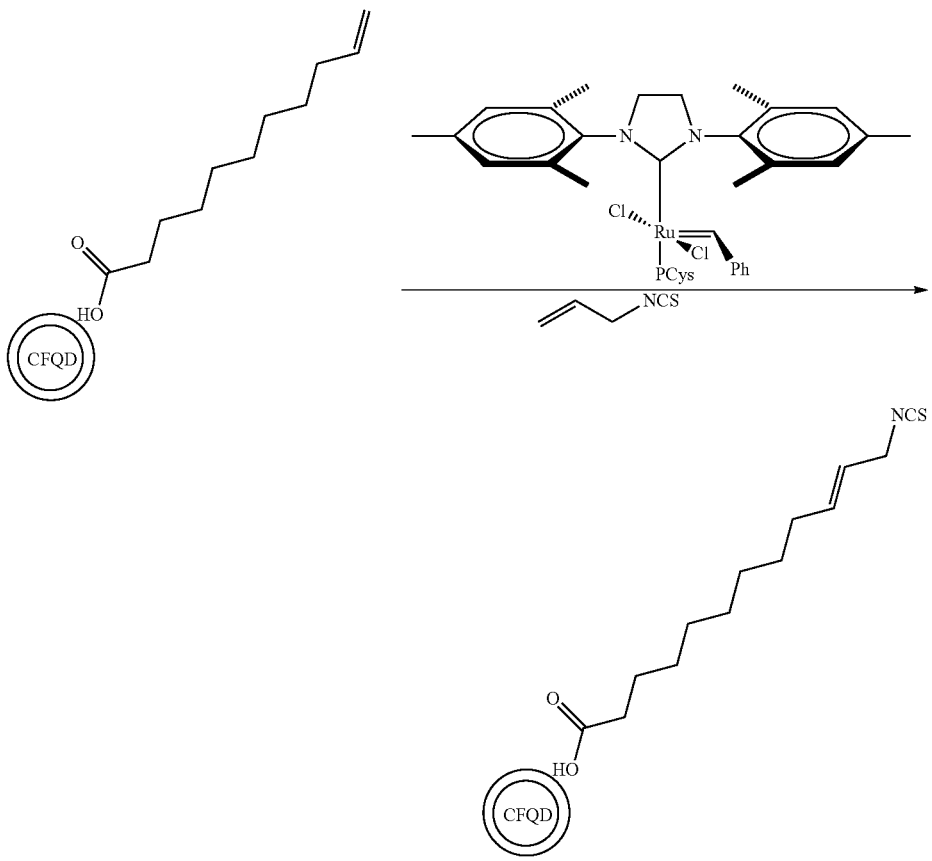

Scheme 2. Schematic description of the procedure.

Solvents were dried and degassed by standard methods unless otherwise stated. Chemicals were obtained from Aldrich, UK (reagent grade) and were used as received unless otherwise stated. Reactions were carried out under a nitrogen atmosphere using standard Schlenk line techniques. A toluene solution (0.45 ml) of CFQD (approx. 50 mg) capped with undecylenic acid (approx. 18.5 mg, 0.17 mmol) was diluted by adding neat toluene (5 ml), followed by allyl isothiocyanate (50 µl, 0.51 mmol). Thereafter, a toluene solution (1 ml) of Grubbs second generation catalyst (5 mol %) was added to the reaction mixture. After refluxing for 68 h, the nanoparticles were precipitated using methanol in a ratio of 1:4, collected by centrifuging at 4,500 rpm for 15 minutes and then dried under nitrogen. The supernatant was decanted and analyzed using GC-MS. The nanoparticles were redissolved in toluene (10 ml). The precipitated nanoparticles were characterized by IR (KBr disk, cm$^{-1}$): 2130, 2077 (NCS), fluorimetry ($\lambda_{max}$ 510 nm).

Loading of the Nanoparticles onto the Substrate Bearing the Fingerprints

The substrate bearing the fingerprints was a glass microscope slide. Preparation of the microscope slides were carried out as follows. An oily finger was pressed onto one side of the microscope slide surface leaving behind an oily fingerprint. A toluene solution (suspension) of prepared nanoparticles (prepared as described above) was taken up into a glass pipette and three large drops were directly placed onto the fingerprint. The microscope slide was carefully maneuvered in order for the nanoparticle solution to completely cover the fingerprint. The solution on the slide was left to partially air dry and then gently heated using a hairdryer for approximately 20 seconds to complete the drying procedure. The sample was illuminated using the LED light source, image was collected through a 495 nm long pass filter and recorded using a digital camera; Fujifilm FinePix S5 Pro. In the middle of a microscope slide, an image of a fingerprint was seen. Both the outline and fingerprint ridge detail were shown very clearly. Since the concentration of the modified yellow nanoparticles was low, the image appeared blue which was due to a manifestation of the light source/filter combination. Also, a thin coating of nanoparticles appeared to be sticking to the microscope slide (around the fingerprint).

EXAMPLE 12

As example 11 but, after imaging, the microscope slide was washed with neat toluene (1 ml) by dripping the toluene onto the sample. After the first toluene wash, the same drying procedure (Example 1) was applied and the microscope slide was imaged and recorded exactly as in Example 11 (FIG. 10a). The same microscope slide was thereafter washed a further two times, dried and imaged (FIG. 10b) and washed an additional three times, dried and imaged (FIG. 10c). Therefore, the microscope slide was washed a total of six times with neat toluene (1 ml).

EXAMPLE 13

Same as example 11 except that in the metathesis reaction, the Hoveyda-Grubbs second generation catalyst is used in place of Grubbs second generation catalyst. The reaction mixture was refluxed at 40° C. for 16 h. Also, the concentration of nanoparticle solution used to tag the oily fingerprint is 1 mg/ml. The sample was illuminated using the LED light source, image was collected through a 495 nm long pass filter and recorded using a digital camera; Fujifilm FinePix S5 Pro and clearly showed an image of a fingerprint outline and ridge detail. The sample was also recorded using a Nikon Coolpix 950 digital camera attached to an Olympus microscope which was used to image the sample in both optical (reflectance) and fluorescence (transmission) modes and showed a section of a nanoparticle tagged fingerprint. The fingerprint ridges are evenly spaced and appear as lines across the image. Fingerprint troughs were clearly seen, i.e. absence of lines. On close inspection, the lines were comprised of small polymeric clumps of nanoparticles, which were binding to the fingerprint ridges. The fingerprint ridges were fluorescent.

The invention claimed is:

1. A conjugate comprising:
a nanoparticle attached to a linker group having a terminal reactive moiety;
wherein said conjugate is of formula II:

$$Q\text{-}A^2(R_1\text{—}B)_m \qquad \qquad II$$

wherein Q is a nanoparticle;
$R_1$ is a saturated or unsaturated $C_{1\text{-}50}$ hydrocarbon chain, optionally interrupted by one or more of —O—, —S—, —NH—, or —$NR_x$— groups, where $R_x$ is a saturated or unsaturated $C_{1\text{-}20}$ alkyl chain, optionally containing O, S, NH or NR;
B is —NCS; and
m is 1; and $A^2$ is —O—, —S—, —C(=O)—, —O—C(=O)—, —C(=O)—O—, —NH—, —NR—, —P(=O)—, —P(=S)—, —P(=O)($R_2$)—, —P(=S)($R_2$)—, —P($R_2$)$_2$— or —P($R_2$)$_3$—, where each $R_2$ is independently selected from OH, OR or R; or
m is 2 and $A^2$ is N, P=O, P=S, P($R_2$) or P($R_2$)$_2$; or
m is 3 and $A^2$ is —O=P, —S=P, —P, —P($R_2$);
where R is a $C_{1\text{-}20}$ alkyl chain, optionally containing O, S, NH or NR and/or optionally containing one or more double or triple bonds; and
wherein said nanoparticle comprises a core of a first semiconductor material having a first luminescence and a shell of a second material which at least partially surrounds the core.

2. The conjugate as claimed in claim 1, wherein group A is attached to the nanoparticle, m is 1, and group $R_1$ is a saturated $C_6\text{-}C_{24}$ group or an unsaturated $C_6\text{-}C_{24}$ group having one double bond.

3. The conjugate as claimed in claim 2, wherein group $A^2$ is a carboxylate group.

4. The conjugate as claimed in claim 1, wherein the first semiconductor material is able to fluoresce.

5. The conjugate as claimed in claim 1, wherein the second material is an insulator or is a semiconductor having a wider band-gap than that of the first semi-conductor material.

6. The conjugate as claimed in claim 1 for the detection of latent fingerprints.

7. The conjugate as claimed in claim 1, wherein the conjugate is in the form of a solution or suspension.

8. The conjugate as claimed in claim 1, wherein the conjugate is in the form of a dry powder.

* * * * *

UNITED STATES PATENT AND TRADEMARK OFFICE
CERTIFICATE OF CORRECTION

PATENT NO. : 8,377,714 B2  Page 1 of 1
APPLICATION NO. : 12/997417
DATED : February 19, 2013
INVENTOR(S) : Cole-Hamilton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 76 days.

Signed and Sealed this
First Day of September, 2015

Michelle K. Lee
*Director of the United States Patent and Trademark Office*